United States Patent [19]
Burack et al.

[11] Patent Number: 5,165,959
[45] Date of Patent: Nov. 24, 1992

[54] METHOD OF MAKING TRIAZINE OPTICAL WAVEGUIDES

[75] Inventors: John J. Burack, Toms River; Treliant Fang, Lawrenceville; Jane D. LeGrange, Princeton, all of N.J.; Jose A. Ors, New Hope, Pa.

[73] Assignee: AT&T Bell Laboratories, Murray Hill, N.J.

[21] Appl. No.: 797,632

[22] Filed: Nov. 25, 1991

Related U.S. Application Data

[63] Continuation-in-part of Ser. No. 748,375, Aug. 22, 1991, abandoned, which is a continuation-in-part of Ser. No. 525,947, May 18, 1990, Pat. No. 5,045,364.

[51] Int. Cl.⁵ .............................................. B05D 5/06
[52] U.S. Cl. .................................... 427/162; 156/643; 427/259; 427/264; 427/346; 427/385.5; 427/404; 427/407.1
[58] Field of Search ............... 427/162, 259, 404, 264, 427/407.1, 346, 385.5; 156/643

[56] References Cited

PUBLICATIONS

"Evaulating Polyimides as Lightguide Materials", by R. Reuter et al., *Applied Optics*, vol. 27, No. 21, Nov. 1, 1988, pp. 4565-4570.

*Primary Examiner*—Bernard Pianalto
*Attorney, Agent, or Firm*—R. B. Anderson

[57] ABSTRACT

An optical waveguide (11) is composed substantially entirely of triazine. Various methods for making desired triazine waveguide patterns are described.

10 Claims, 1 Drawing Sheet

5,165,959

METHOD OF MAKING TRIAZINE OPTICAL WAVEGUIDES

This is a continuation-in-part of the patent application of Burack et al., Ser. No. 07/748,375 filed Aug. 22, 1991, now abandoned, which, in turn, is a continuation-in-part of the patent application of T. Fang, Ser. No. 07/525,947 filed May 18, 1990, U.S. Pat. No. 5,045,364 which is hereby incorporated herein by reference.

TECHNICAL FIELD

This invention relates to polymer optical waveguides.

BACKGROUND OF THE INVENTION

The publication, "Evaluating Polyimides as Lightguide Materials," by R. Reuter et al., *Applied Optics*, Vol. 27, No. 21, Nov. 1, 1988, pp. 4565–4570, describes the use of a number of different polymers as media for transmitting lightwaves. Various polymer materials such as polymethyl methacrylate and various polyimides have been proposed as materials from which lightguide or optical waveguide patterns can be made on a flat substrate. Such films may be only a few microns in thickness and can be used to transmit light to optoelectronic devices on a substrate much the way printed circuits transmit electrical current on a printed wiring board. Effective transmission requires that the optical waveguide material have a relatively low attenuation or loss with respect to the light beam transmitted and that it have a higher optical index of refraction than the surrounding media. The materials mentioned in the paper have a sufficiently high index of refraction and a sufficiently low loss, at least at certain optical frequencies, to be useful as practical media for optical waveguide purposes.

The article points out that a major disadvantage of polymethyl methacrylate is its poor thermal and environmental stability. Disadvantages of polyimides include their high cure temperature, typically above three hundred degrees Centigrade, which could be damaging to certain substrates such as printed wiring boards made of commonly used resin materials, and their relatively high cost.

There is therefore a continued long-felt need for polymer waveguides that can transmit light with low loss and high efficiency, that have good thermal and environmental stability, can be made without subjecting them to inordinately high cure temperatures, are of low cost, and are amenable to mass production.

SUMMARY OF THE INVENTION

In accordance with the invention, we have found that practical optical waveguides may be made of triazine polymers (also known as polycyanate resins). Such waveguides do not require excessively high temperatures in their fabrication, are of lower cost than polyimides, have high temperature and environmental stability, and can be efficiently manufactured in printed circuit form.

These and other objects, features, advantages of the invention will be better understood from a consideration of the following detailed description taken in conjunction with the accompanying drawing.

DETAILED DESCRIPTION

Figure 1:
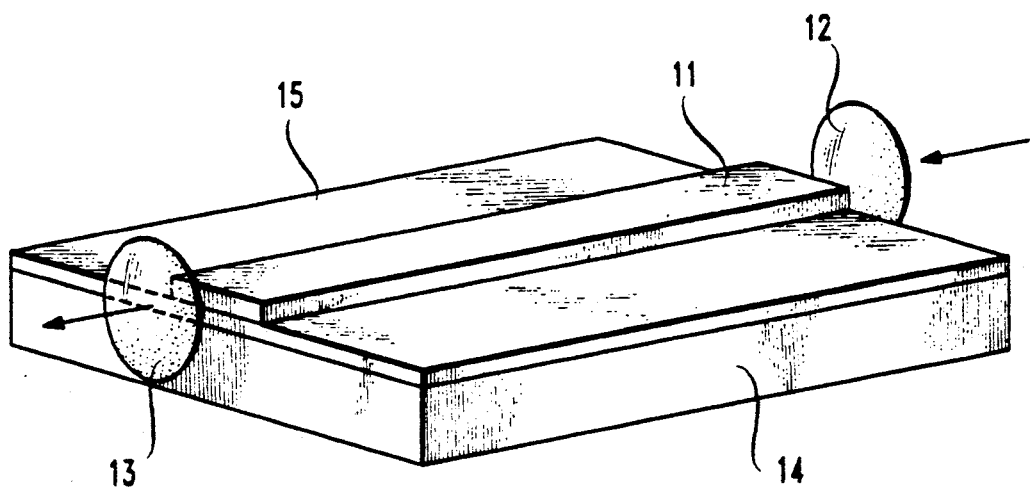
FIG. 1 is a schematic perspective view of an optical waveguide in accordance with an illustrative embodiment of the invention.

Referring now to FIG. 1, there is shown schematically an optical waveguide 11 used for propagating light from one end thereof to the other, as shown by the arrows. Lenses 12 and 13 are typically used to apply light to and remove light from the waveguide 11. In accordance with the invention, the waveguide 11 is substantially completely composed of cured triazine. The waveguide 11 is supported on a substrate 14 upon which is formed a layer 15 of low refractive index material. The two primary requirements for an optical waveguide is that it must have a higher refractive index than the surrounding media and it must have a low attenuation or loss with respect to the transmitted light. Triazine has a typical refractive index of approximately 1.6, which is sufficiently high to be higher than any of various materials that could be used as a cladding. For the experimental use shown, the "cladding" on three sides of the waveguide is air which has a refractive index of 1.0. The layer 15 may be of glass which has a much lower refractive index than triazine. It is to be noted that in commercially useful devices, the waveguide 11 would typically be used to transmit light to and from any of various optoelectronic devices or passive components such as couplers; these various known uses for optical waveguides have not been illustrated in the interest of brevity and simplicity. The waveguide itself can constitute a passive device such as a coupler, a power combiner, or a power divider, as is known.

Figure 2:
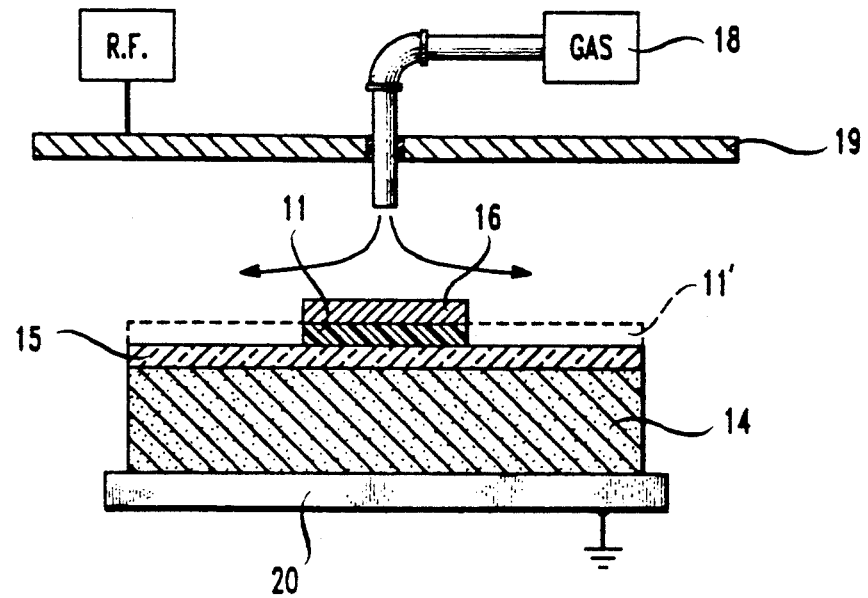
FIG. 2 is a schematic view of apparatus that may be used for making the device of FIG. 1.

An advantage of using triazine as a waveguiding material is that waveguide circuits of triazine can be easily and conveniently made and are amenable to mass production. Referring to FIG. 2, a waveguide pattern can be made by applying over the entire surface of layer 15 a layer 11' of triazine that may have a typical thickness of two microns. Over this, a layer of aluminum is applied, which is patterned by known photolithographic masking and etching to yield an aluminum mask 16 having a configuration corresponding to that of the desired waveguide pattern. The triazine can then be etched in a standard plasma etch reactor, which is shown schematically in FIG. 2. Gas from a source 18 is directed into the space between electrodes 19 and 20, as shown by the arrows. A radio frequency plasma is then formed between electrodes 19 and 20 which enhances a reaction of the gas with the triazine to etch away the unmasked portion of the layer 11', shown by the dotted lines, thereby to leave an etched layer 11 having a configuration conforming to the desired waveguide pattern.

Waveguides such as waveguide 11 of FIG. 1 have been made using commercially available triazine monomer solutions in methyl ethylketone. One of the compounds is known as Arocy F-40S, which is a fluorinated monomer, and the other is REX-368, which is not fluorinated, both of which are available from Hi-Tek Polymers of Louisville, Ky. The triazine compound was diluted to approximately thirty-five percent solids in polypropylene gycol methyl ether acetate (PGMEA). A surfactant, FC-430, commercially available from the 3M Company of Minneapolis, Minn., was added to a concentration of 0.02 percent by weight to insure even spreading of the solutions on the substrate.

The substrate 14 was a silicon wafer, with layer 15 being of silicon dioxide. To insure good adhesion between the monomer film and the substrate, an adhesion promoter comprising 0.05 weight percent 3-aminopropyltrimethoxysilane, ninety-five weight percent methanol and 4.95 percent water was deposited on the surface of layer 15. The triazine monomer was deposited to a thickness of 2.0 microns by spinning the substrate at two thousand rotations per minute for thirty seconds. Curing was done in a glass tube furnace under a nitrogen purge. The curing steps were as follows:

1. One degree Centigrade per minute ramp to one hundred twenty degrees Centigrade.
2. Dwell at one hundred twenty degrees Centigrade for one hour.
3. Ramp at three degrees Centigrade per minute to two hundred thirty degrees Centigrade.
4. Dwell two hours at two hundred thirty degrees Centigrade.
5. Allow to cool overnight in the furnace under a nitrogen purge.

After the triazine film was cured, aluminum was sputtered to a thickness of approximately two thousand three hundred angstroms using a commercially available sputtering machine. Photoresist was spun over the aluminum, the photoresist was baked dry, and the waveguide pattern was imaged using a commercially available contact printer. The photoresist was developed and the exposed aluminum removed in a standard aluminum acid etch. The films were placed in the reactive ion etcher, as shown schematically in FIG. 2, which was a PlasmaLab model, available from the Plasma Technology Company of Avon, England. The triazine 11' was etched at one hundred watts of power and one hundred millitorr pressure in an atmosphere of twenty percent Freon and eighty percent oxygen. After etching, the remaining photoresist and aluminum was removed from the wafer to yield the structure of FIG. 1.

Both of the triazines that were tested had an optical loss of less than three db per centimeter at an optical transmission wavelength of 632.8 nanometers. The fluorinated triazine had a refractive index of 1.5303 at 632.8 nanometers. The unfluorinated triazine had a refractive index of 1.606 at 632.8 nanometers and 1.588 at 1064 nanometers. The films were capable of withstanding temperatures of approximately three hundred degrees Centigrade, which indicates good thermal stability. As pointed out in the aforementioned Fang patent application, a reason for the inherent thermal and environment stability of triazine is that it is cross-linked in three dimensions, which is unlike PMMA, a thermoplastic material without cross-linking capability. It is believed that the curing temperature of the triazine can be lowered to be less than two hundred degrees Centigrade if this is needed to prevent damage to the substrate 14 during processing. As mentioned before, certain printed wiring boards have a resin composition which is incapable of withstanding the high temperatures required, for example, for curing polyimide.

The foregoing are only examples of methods for making triazine waveguides. A generalized process for making such waveguides is as follows:

1. Preparation of the Precursor Solution

The triazine precursor may be dissolved in a number of organic solvents such as methyl ethyl ketone (MEK) or propylene glycol methyl ether acetate (PGMEA). The concentration of the solution will depend upon the desired thickness of the film and the method of application to the substrate. Various additives may be mixed into the solution to improve processability, such as surfactant to improve spreadability or catalysts to decrease cure time or temperature. Examples of surfactants include 3M Corporation's FC-430 material; catalysts include metal complexes such as zinc octanoate and organic amines such as N,N dimethylbenzylamine.

2. Preparation of the Substrates

Substrate preparation may include a chemical and/or plasma clean. If the supporting substrate does not already contain a top lower index of refraction cladding layer, it may be applied at this point. If laser writing is the method used to etch the triazine film, and the supporting substrate consists of a material that can be damaged from the laser, a thin reflective metal coating may be applied between the substrate and the low index cladding layer. An adhesion promoter may also be applied to improve adhesion between the triazine film and the low index cladding layer.

3. Application of Triazine Precursor Solution to the Substrate

There are two methods which may be used to apply the precursor solution to the substrate: spin-coating or spray coating.

Spin-coating is usually used to obtain film thickness of 25 $\mu$m or less. In this method, the solution is applied to the center of the substrate; the substrate is then rotated at high speeds causing the material to spread out in all directions on the substrate. The actual thickness achieved is dependent upon the concentration of the precursor solution, the solvent system of the precursor solution, the speed of rotation, and the time interval under rotation.

Spray coating is usually used to obtain film thickness of 10 $\mu$m or greater. In this case, the precursor solution is forced through a spray nozzle onto the substrate. The actual thickness achieved can be dependent upon precursor solution concentration, the solvent system used, the atomization pressure, and the spray nozzle configuration.

4. Cure of the Precursor Solution

The precursor solution is preferably thermally cured under nitrogen. The bake temperature should not exceed 300° C. The exact bake times and temperature will depend on the thickness of the films and the amount of catalyst mixed into the solution.

5. Application of the Etch Mask

The main requirement for a material to act as an etch mask is that it be able to protect the underlying triazine film from erosion during the triazine etch process. This can be accomplished by applying a thin coat of a material that is either etch resistant or etches at a slower rate than the triazine so that the exposed triazine areas are etched away before the mask material. If the mask material were to etch at a similar or faster rate than the triazine, it must be applied thick enough so that a portion of the mask remains after all exposed regions of triazine are removed. Two examples of materials that are etch resistant or which etch slowly are metals and ceramics. In some cases, the photoresist to be used may be sufficiently resistant to the triazine etch so a separate etch mask may not be needed. In such a case, this step may be omitted.

5.1. Metal Etch Masks

Metal etch masks may include materials such as aluminum, chromium, and copper. The material may be applied to a thickness of several thousand angstroms by sputtering or evaporation methods.

5.2. Ceramic Etch Masks

Ceramics may be applied as either spin on glasses (SOG), by chemical vapor deposition (CVD) methods or sputtering.

SOG are materials such as siloxane compounds which may be purchased from a variety of commercial sources. These materials are spun onto the triazine film, and then baked to allow crosslinking. Baking should not be done at temperatures above 300° C. or damage to the triazine may result. The exact bake times and thickness of the SOG film is dependent upon the etch resistance desired.

Ceramics such as silicon dioxide and silicon nitride may be applied by CVD or sputtering methods. The thickness of the mask required will vary based upon the quality of the ceramic film and the composition of the etch gases.

6. Application, Definition, and Development of the Photoresist

The photoresist serves one of two purposes: it either can be used to protect areas of the mask from attack during the etching of the mask to expose the underlying triazine film, or, if it is resistant enough to the triazine etch conditions, it can be used as the mask itself, eliminating the need for the application of a separate etch mask described in the previous step.

Almost any photoresist can be used. The actual procedure for application, definition and development of the photoresists will depend upon the material chosen. Most photoresists are coated onto the substrate, the material is then baked to drive out the solvent, and exposed, usually to ultraviolet radiation under a mask that blocks some areas of the resist from exposure. The image is then developed, which removes either the exposed or unexposed areas of the resist. Most developing procedures are "wet" in nature requiring the resist be exposed to either organic solvents or some liquid chemical solution. An example of this type of material is the commercially available Shipley 1400-31 positive resist. Some photoresists, such as certain polysilane materials, may also be plasma developed in a reactive ion etcher (RIE). If the photoresist chosen is also to act as the triazine etch mask, this offers the advantage of performing two sequential steps of the process (the development of the resist and the etching of the triazine) in the same chamber.

7. Etching of the Etch Mask

The exact procedure for etching the mask will depend on the type of mask that is used. For metal masks, most etch solutions can be purchased commercially. Examples include C.A.N. etch for chromium manufactured by Photochemical Supply in Fairfield, N.J. and Aluminum etch manufactured by the Baker Chemical Company in Phillipsburg, N.J.

Many CVD or sputter deposited ceramic masks can be etched in solution of hydrofluoric acid and water. The exact concentration and temperature of the solution will depend on the etch rate desired.

Most SOG materials may be etched in the RIE in an atmosphere of a fluorinated gas such as FREON (a trademark of the DuPont Company). CVD and sputter deposited ceramics may also be etched this way.

8. Etching of the Triazine

The purpose of the triazine etch is, of course, to remove areas of the film while preserving others so that the proper waveguide configuration may be obtained. There are three methods which may be used for etching triazine: laser writing, reactive ion etching, and ion milling. Whichever method is used, care must be taken to keep the side walls as smooth as possible. Rough side walls will promote light scattering, thus increasing the loss of the waveguide.

8.1. Reactive Ion Etching and Ion Milling

Reactive ion etching and ion milling are two variations of the same process. In reactive ion etching, a plasma is produced in gases that are chemically reactive with the triazine. Chemical reactions occur between these gases and the triazine which etches the film. Gases used for the reactive ion etching of triazine are pure oxygen or some combination of oxygen and fluorinated gases such as FREON. Care must be taken when using fluorinated gases with ceramic etch masks since such gases will also erode the etch mask.

In ion milling or sputter etching, a non-reactive gas such as argon is used. A plasma is produced in the etching chamber, and ions are accelerated toward the substrate where the surface is eroded by momentum transfer.

8.2. Laser Writing

Laser writing offers an advantage over the plasma etch methods because no etch mask is needed so it can considerably shorten the process steps required. Two types of laser writing mechanisms may be used: laser ablation, and laser pyrolysis.

Laser ablation uses a highly focused excimer laser. The beam of the laser locally breaks chemical bonds in the triazine film causing an area of the film to be vaporized. Laser pyrolysis uses a carbon dioxide laser. The laser locally heats up the triazine film causing areas of the film to be burned away. In both cases, the film may be etched by selectively allowing the laser beam to come into contact with the areas of the film that are to be removed.

9. Removal of the Remaining Photoresist and Etch Mask

After the triazine is etched, any remaining photoresist and the etch mask may be removed from the surface of the waveguide. If a ceramic etch mask is used, and the material has a lower index of refraction than the underlying triazine layer, the material may remain as a protective coating on top of the triazine waveguide if its presence does not adversely affect the optical loss.

The embodiments shown are intended to be merely illustrative of the concepts of the invention. For example, the triazine can be made from a synthesized monomer as described in detail in the aforementioned Fang application. Various other embodiments and modifications may be made by those skilled in the art without departing from the spirit and scope of the invention.

We claim:

1. A method for forming a desired optical waveguide pattern comprising the steps of:
   putting a quantity of fluid triazine precursor on a substrate;
   spinning the substrate to make a film of the triazine precursor;
   curing the precursor to form cross-linked triazine polymer, the curing comprising the step of heating the substrate;
   forming over the triazine polymer a layer of aluminum;

forming a pattern in the aluminum layer corresponding to said desired pattern;
subjecting the triazine polymer to a plasma etch using the patterned aluminum layer as a mask;
and removing the aluminum layer.

2. The method of claim 1 wherein:
the triazine precursor is a fluorinated triazine precursor.

3. The method of claim 1 wherein:
prior to applying the fluid triazine, a quantity of 3-aminopropyltrimethoxysilane is applied as a film to the substrate for promoting the adhesion of the triazine film to the substrate.

4. A method for forming an optical waveguide pattern comprising the steps of:
forming a film of fluid triazine precursor on a substrate;
curing the precursor to form cross-linked triazine polymer, the curing comprising the step of heating the substrate;
forming over the triazine polymer a masking layer;
forming a pattern in the masking layer corresponding to said optical waveguide pattern;
and etching the triazine polymer using the patterned masking layer as a mask.

5. The method of claim 4 further comprising the step of:
removing the masking layer.

6. The method of claim 5 wherein:
the masking layer is a metal mask.

7. The method of claim 5 wherein:
the etching step comprises the step of plasma etching triazine polymer.

8. The method of claim 7 wherein:
the mask is an aluminum mask.

9. The method of claim 8 wherein:
the film forming step comprises the step of depositing the fluid triazine on the substrate and then spinning the substrate.

10. The method of claim 8 wherein:
the film forming step comprises the step of depositing the fluid triazine on the substrate by spraying.

* * * * *